United States Patent [19]

Wiener

[11] 4,203,219
[45] May 20, 1980

[54] DENTAL MODEL ASSEMBLY AND PRODUCTION METHOD

[75] Inventor: Joseph Wiener, Dayton, Ohio
[73] Assignee: Carl Dorf, Walnut Creek, Calif.
[21] Appl. No.: 931,943
[22] Filed: Aug. 8, 1978
[51] Int. Cl.$^2$ .............................................. A61C 13/00
[52] U.S. Cl. ..................................................... 433/74
[58] Field of Search ................................. 32/11, 40 R
[56] References Cited

U.S. PATENT DOCUMENTS

| | | | |
|---|---|---|---|
| 3,436,827 | 4/1969 | Dew | 32/11 |
| 3,478,428 | 11/1969 | Stengel | 32/11 |
| 3,581,398 | 7/1971 | Thomas | 32/11 |
| 3,702,027 | 11/1972 | Marshall et al. | 32/11 |
| 4,017,972 | 4/1977 | Glenn | 32/11 |
| 4,021,916 | 5/1977 | Spalten | 32/11 |

*Primary Examiner*—Robert Peshock
*Attorney, Agent, or Firm*—Jacox & Meckstroth

[57] ABSTRACT

A U-shaped die locator is molded of a plastics material and has a tapered rib portion with non-uniformly spaced and laterally extending grooves on opposite sides of the rib portion. The rib portion is inserted into a settable model material which is poured into a negative dental impression to form a positive model. The die locator has a second or channel portion which is embedded within a settable base material poured onto the model to form a base for the model. After the base material hardens, the model is separated from the base and the rib portion, and the model is cut into model dies or sections which are reseated on the rib portion and the base. The die locator may also be molded with integral small diameter support pins which may be used for positioning the die locator within the negative impression by a conventional pin setter or support device.

22 Claims, 8 Drawing Figures

U.S. Patent　　May 20, 1980　　4,203,219
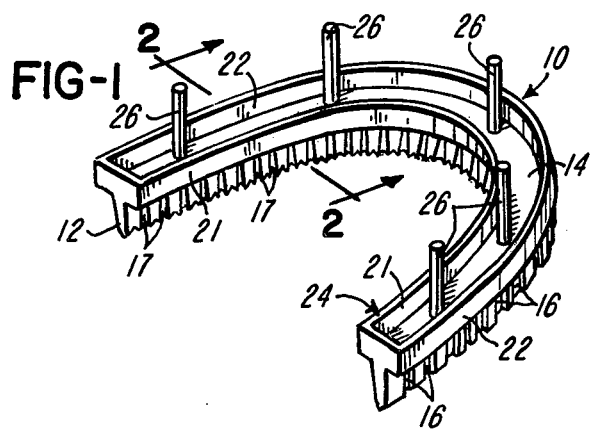
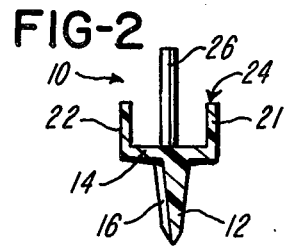
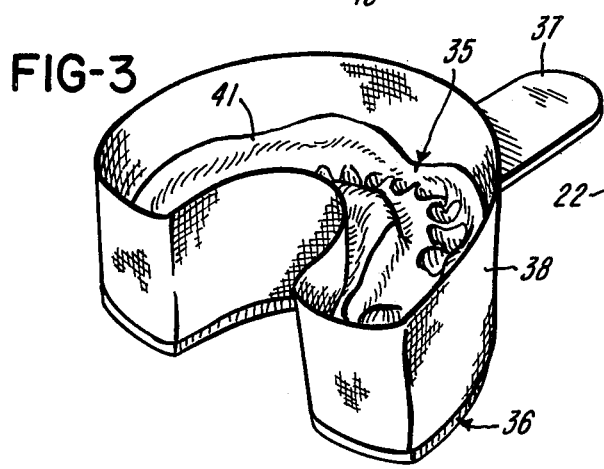
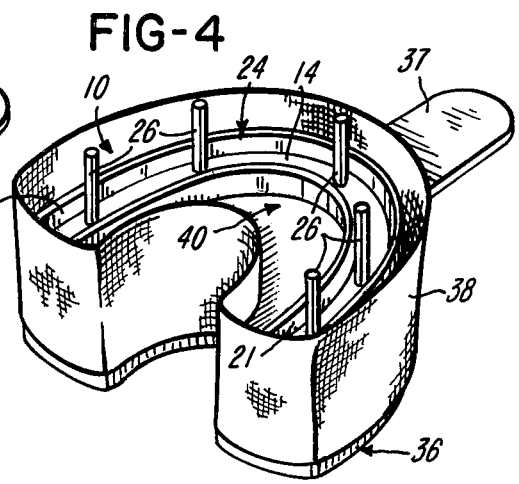
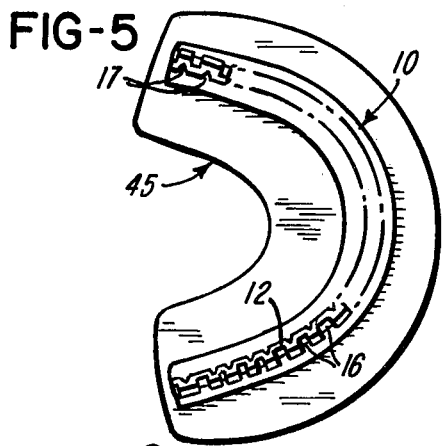
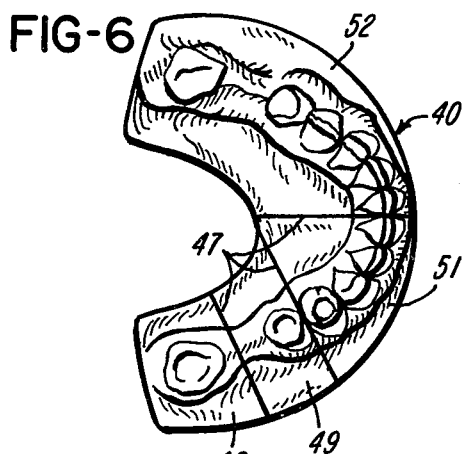
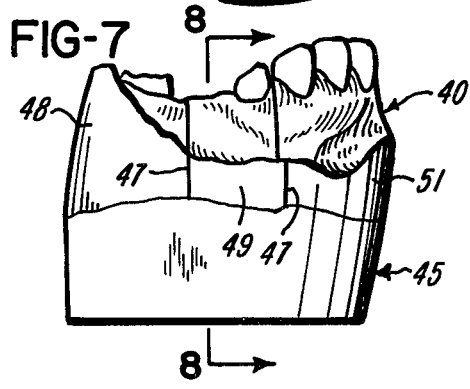
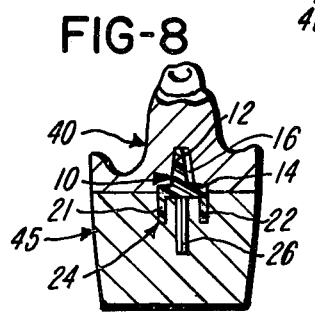

DENTAL MODEL ASSEMBLY AND PRODUCTION METHOD

BACKGROUND OF THE INVENTION

In the production of dental restorations such as inlays, crowns, bridges and the like, there have been a number of devices and procedures either developed or proposed for eliminating the use of individual tapered dowel pins for locating the removable dies which are formed by cutting a dental model into sections. Such individual dowel pins are small and difficult to handle, and some form of apparatus, for example, as disclosed in U.S. Pat. No. 4,017,972, is required for positioning the pins within a dental model. Examples of such proposed devices and procedures are disclosed in U.S. Pat. Nos. 3,436,827 and 3,702,027. In these devices, a positive dental model is formed in a conventional manner and then the model or a section of the model is shaped and connected to a moldable base material which is received within a locating tray. When the base material hardens to form a base for the model, the combined model and base are removed from the tray so that the model and base may be cut into sections or separate dies which are placed back into the tray in their original orientation.

Another form of device developed for eliminating the need for individual tapered dowel pins is disclosed in U.S. Pat. No. 3,478,428. In this patent, a plurality of tapered pins are molded of a plastics material and are integrally connected by a base portion which is embedded in and positively connected to the dental model. The base portion is cut into sections when the model is cut into dies so that each die is provided with one or more tapered locating pins which seat within corresponding tapered sockets or holes formed within the molded support base for the model. U.S. Pat. No. 3,581,398 discloses another form of die locator wherein a U-shaped keying device is embedded within the dental model and has a projecting serrated rib portion which is received within a mating recess formed within the support base for the model. This keying device is also cut into sections when the model is cut into dies so that each die is provided with a section of the keying device for locating the die.

SUMMARY OF THE INVENTION

The present invention is directed to an improved method and apparatus or device for making a dental model assembly and which provides for significantly reducing the time and expense for producing an assembly with conveniently removable and reseatable sections or dies. The method and device of the invention also provide for precisely locating the removable dies so that after each removable die or other portion of the model is reseated on the support base, the model corresponds precisely with the negative dental impression. The apparatus or device further prevents reseating the dies in improper locations and is adapted to be used with different moldable materials commonly used in the dental field, such as dental stone or dental epoxy.

In accordance with one embodiment of the invention, the above features and advantages are provided by an arch-shaped die locator which is molded of a plastics material and includes elongated tapered rib portion havng laterally extending grooves. The grooves are non-uniformly spaced and provide the rib portion with corrugated inner and outer surfaces. The rib portion is integrally molded with a second or channel portion formed by generally parallel spaced walls. The rib portion of the die locator is embedded within the dental model, and the channel portion is embedded within the support base for the model. After the model and base are formed, the model is separated from the base and the rib portion of the die locator and is cut into sections or dies which are then reseated on the corresponding mating sections of the rib portion of the die locator.

Other features and advantages of the invention will be apparent from the following description, the accompanying drawing and the appended claims.

BRIEF DESCRIPTION OF THE DRAWING

FIG. 1 is a perspective view of a die locator constructed in accordance with the invention;

FIG. 2 is a section of the die locator taken generally along the line 2—2 of FIG. 1;

FIG. 3 is a perspective view of a typical full arch negative impression prepared for making a positive model of the impression;

FIG. 4 is another perspective view of the negative impression shown in FIG. 3 after the impression is poured and the die locator shown in FIG. 1 is inserted within the settable model material;

FIG. 5 is a plan view of a support base for the model shown in FIG. 4 and showing the exposed rib portion of the die locator after the model has been separated from the base;

FIG. 6 is a plan view of the dental model which has been removed from the die locator base shown in FIG. 5 and after having been cut into sections and dies;

FIG. 7 is a side view of the reassembled dies and support base; and

FIG. 8 is a section of the reassembly as taken generally on the line 8—8 of FIG. 7.

DESCRIPTION OF THE PREFERRED EMBODIMENT

FIG. 1 illustrates a die locator 10 which is molded of a thermoplastics material and which incorporates an elongated arch or U-shaped body including a first or rib portion 12 projecting from a flange portion 14. The rib portion 12 has a tapering cross-sectional configuration (FIG. 8) and has an inclined outer surface which is interrupted by longitudinally spaced and laterally extending or vertical grooves 16. The inclined inner surface of the rib portion 12 is also interrupted by longitudinally spaced and laterally extending or vertical grooves 17 which are staggered with respect to the grooves 16 and cooperate therewith to provide the rib portion 12 with a corrugated longitudinal configuration. The spacing of the grooves 16 and the spacing of the grooves 17 is non-uniform so that any small section of the rib portion 12 is unique and not identical with any other similar section of the rib portion. The height of the rib portion 12 is between 0.20 and 0.37 inch and preferably about 0.28. inch.

A set of spaced inner and outer walls 21 and 22, respectively, project from the flange portion 14 and cooperate therewith to form an arch-shaped channel portion 24. The die locator 10 also includes a series of longitudinally spaced cylindrical pins 26 which project outwardly or upwardly from the center of the flange portion 14 above the walls 21 and 22.

FIG. 3 of the drawing illlustrates a typical full arch negative impression 35 which is supported and carried by a plastic impression tray 36 having a handle portion 37. The U-shaped impression 35 is surrounded by a border 38 which is preferably formed of masking tape, but may be formed from other flexible material such as a thin wax sheeting. The masking tape border 38 overlaps the support tray 36 and is sealed to the impression 35 by a fillet 41 of wax which extends around the periphery of the negative dental impression 35.

In the construction of a positive model of the negative impression 35, one or both of the end portions of the die locator 10 are cut, if necessary, and removed to form the desired arcuate section which corresponds to the impression 35. The impression 35 is filled with a setable material such as dental stone or epoxy until the top surface of the material is generally level with the wax fillet 41. The pretrimmed die locator 10 is then pressed into the settable material within the impression 35 until the flange portion 14 contacts the material. If desired, the support pins 26 may be used to position and suspend the die locator 10 within the impression 35 at the desired elevation by means of a conventional pin setter. However, the relative light weight of the die locator 10, as a result of the channel portion 24, prevents an unsupported die locator from sinking into lower density model materials such as epoxy.

After the dental stone or epoxy hardens within the negative impression 35, the material forms a positive model 40 (FIG. 4) with the walls 21 and 22 and the pins 26 projecting upwardly above the top or base surface of the model 40. A hardenable or settable base material, such as dental stone, is then poured into the cavity above the model 40 and defined by the masking tape border 38. The material is preferably poured until it completely covers the pins 26 which also serve as a level indicator.

After the base material hardens to form a base 45 (FIG. 5), the masking tape border 38 is removed, and the assembly of the model 40, base 45 and interconnecting die locator 10 is removed from the support tray 36. The model 40 is then released and separated from the base 45 and from the tapered rib portion 12 of the die locator 10. As illustrated in FIG. 5, the die locator 10 remains permanently attached to the base 45 as a result of the channel portion 24 being permanently embedded within the rigid base 45. As shown in FIG. 6, after the one piece model 40 is separated from the base 45 and the die locator 10, the model 40 is cut along lines 47 to form the model dies 48 and 49 and model sections 51 and 52. The model dies 48 and 49 and sections 51 and 52 are then reseated back onto the corresponding portions of the die locator 10 and the base 45, as illustrated in FIGS. 7 and 8.

From the drawing and the above description, it is apparent that the method and apparatus for making a dental model assembly in accordance with the invention significantly simplifies and reduces the time for constructing a dental model assembly. As another important advantage, the tapered rib portion 12 of the die locator 10 positively and precisely locates each model die when the die is reseated back on the die locator 10 and the base 45, as shown in FIG. 8. This precision and positive location results from the rigidity of the rib portion 12 and the positive locking of the die locator 10 into the base 45 by the channel portion 24. Furthermore, the non-uniform spacing of the grooves 16 and 17 within the rib portion 12 assures that even very thin or narrow dies cannot be inadvertently reseated in an improper position on the base 45.

As mentioned above, any longitudinal portion of the die locator 10 may be used in the production of a corresponding dental model. For example, only one side or end portion of the die locator would be used in making a quadrant model and dies. Furthermore, while the method and form of die locator herein described constitute a preferred embodiment of the invention, it is to be understood that the invention is not limited to the precise method and form of apparatus described, and that changes may be made therein without departing from the scope and spirit of the invention as defined in the appended claims.

The invention having thus been described, the following is claimed:

1. A die locator for use in making a dental model assembly, comprising an elongated generally U-shaped body of solid material, said body including a longitudinally extending generally U-shaped rib portion having converging opposite side surfaces forming a tapering cross-sectional configuration, said rib portion adapted to project into a molded dental model and being releasable therefrom, said body including means for rigidly connecting said rib portion to a base disposed to support the model, and said rib portion having means for precisely locating individual sections of the dental model after the model is cut into sections and for preventing longitudinal movement of each section on said rib portion.

2. A die locator as defined in claim 1 wherein at least one of said side surfaces of said rib portion has longitudinally spaced and laterally extending grooves.

3. A die locator as defined in claim 3 wherein said grooves are non-uniformly spaced along said one side surface of said rib portion.

4. A die locator as defined in claim 1 wherein said body further includes a longitudinally extending flange portion projecting laterally from said rib portion.

5. A die locator as defined in claim 1 wherein said connecting means comprises a U-shaped channel portion projecting from said rib portion and having generally parallel spaced arcuate walls.

6. A die locator as defined in claim 1 including a plurality of longitudinally spaced pins formed as an integral part of said body, and said pins project upwardly from said connecting means.

7. A die locator as defined in claim 1 wherein said body comprises a solid plastics material.

8. A dental model assembly comprising an elongated die locator having a first locating portion and a second support portion, the second support portion being part of a rigid base, the first locating portion projecting into a solid dental model of moldable material supported by the base, the dental model being separable from both the base and the first locating portion of the dental model and being cut into sections, the first locating portion of the die locator including a longitudinally extending rib portion having laterally converging opposite side surfaces forming a tapering cross-sectional configuration, and the first locating portion of the die locator also having means for precisely locating each section of the dental model at its corresponding position and for preventing longitudinal movement of each section along the die locator.

9. A dental model assembly as defined in claim 1 wherein opposite side surfaces of said rib portion have longitudinally spaced and laterally extending grooves.

10. A dental model assembly as defined in claim 9 wherein said grooves are non-uniformly spaced along said side surfaces of said rib portion.

11. A dental model assembly as defined in claim 8 wherein said first locating portion of said die locator is connected to said second support portion by means including a longitudinally extending and outwardly projecting flange portion.

12. A dental model assembly as defined in claim 8 wherein said second support portion of said die locator comprises an elongated channel portion embedded within a hardened base material forming the rigid base.

13. A method of making a dental model assembly from a negative dental impression, comprising the steps of forming an elongated generally U-shaped die locator including a longitudinally extending rib portion having converging side surfaces defining a tapering cross-sectional configuration, pouring a settable model material into the negative impression, locating the rib portion of the die locator within the model material before the material sets, allowing the model material to set to form a positive model of the impression, forming a base rigidly connected to the rib portion of the die locator and for supporting the model, removing the model from the base and from the rib portion of the die locator, cutting the model into separate dies or sections, and reseating the separate dies or sections back onto the base and onto the rib portion of the die locator in their respective locations.

14. A method as defined in claim 13 and including the step of forming longitudinally spaced and laterally extending grooves within at least one of the side surfaces of the rib portion.

15. A method as defined in claim 14 including the step of forming the grooves with non-uniform longitudinal spacing to assure correct reseating of the separate dies or sections back onto the rib portion of the die locator.

16. A method as defined in claim 14 including the step of forming the grooves within both the inner and outer side surfaces of the rib portion.

17. A method as defined in claim 16 including the step of locating the grooves within the inner side surface of the rib portion in longitudinally offset relation to the grooves within the outer side surface of the rib portion.

18. A method as defined in claim 13 wherein the base is formed by pouring a settable base material onto the model and around a second portion of the die locator.

19. A method as defined in claim 18 including the step of molding a U-shaped channel portion as an integral part of the die locator to form said second portion.

20. A method as defined in claim 13 including the steps of molding a plurality of longitudinally spaced pins as integral parts of the die locator to facilitate locating the die locator within the model material poured into the impression.

21. A method as defined in claim 13 including the step of forming a longitudinally extending flange portion projecting outwardly from said rib portion.

22. A method as defined in claim 21 including the said steps of molding generally parallel spaced walls projecting from the flange portion, and embedding the walls within a settable material forming the base for the model.

* * * * *